US012788380B2

(12) United States Patent
Rebellino et al.

(10) Patent No.: US 12,788,380 B2
(45) Date of Patent: Nov. 10, 2026

(54) USER INTERFACE FOR BIOPSY DEVICE

(71) Applicant: Devicor Medical Products, Inc., Cincinnati, OH (US)

(72) Inventors: Justin Rebellino, Cincinnati, OH (US); David C. McBreen, Cincinnati, OH (US); Andrew P. Nock, Dayton, OH (US); Kyle Wagner, Mason, OH (US); Brennan Gallagher McCabe, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 964 days.

(21) Appl. No.: 17/729,281

(22) Filed: Apr. 26, 2022

(65) Prior Publication Data

US 2022/0249074 A1 Aug. 11, 2022

Related U.S. Application Data

(63) Continuation of application No. PCT/US2020/057466, filed on Oct. 27, 2020.

(60) Provisional application No. 62/926,805, filed on Oct. 28, 2019.

(51) Int. Cl.
*A61B 10/02* (2006.01)

(52) U.S. Cl.
CPC .. *A61B 10/0275* (2013.01); *A61B 2010/0208* (2013.01); *A61B 2560/0487* (2013.01)

(58) Field of Classification Search
CPC ........ A61B 10/0275; A61B 2010/0208; A61B 2560/0487; A61B 34/25
See application file for complete search history.

(56) References Cited

U.S. PATENT DOCUMENTS

| | | | |
|---|---|---|---|
| 5,511,556 A | 4/1996 | DeSantis | |
| 5,526,822 A | 6/1996 | Burbank et al. | |
| 5,560,373 A | 10/1996 | DeSantis | |
| 5,817,033 A | 10/1998 | DeSantis et al. | |

(Continued)

FOREIGN PATENT DOCUMENTS

| | | |
|---|---|---|
| EP | 3103397 | 12/2016 |
| EP | 3669789 | 6/2020 |

(Continued)

OTHER PUBLICATIONS

International Search Report and Written Opinion dated Feb. 2, 2021 for Application No. PCT/US2020/057466, 13 pages.
U.S. Appl. No. 62/916,277, filed Oct. 17, 2019.

*Primary Examiner* — Rene T Towa
(74) *Attorney, Agent, or Firm* — FBT Gibbons LLP

(57) ABSTRACT

A core needle biopsy device includes a needle assembly, a drive assembly, and a user interface. The needle assembly includes a piercer and a hollow cutter. The piercer includes a sharp distal tip and a notch proximal to the distal tip. The piercer is slidably disposed within the cutter to sever a tissue sample into the notch of the piercer. The drive assembly is configured to selectively move the piercer and the cutter. The user interface has a plurality of indicators. Each indicator of the plurality of indicators is configured to independently transition between a plurality of predetermined states to collectively define a plurality of predetermined status sequences that indicate movement of the piercer and the cutter via the drive mechanism.

17 Claims, 9 Drawing Sheets

(56) References Cited

U.S. PATENT DOCUMENTS

| | | | | |
|---|---|---|---|---|
| 6,086,544 | A | 7/2000 | Hibner et al. | |
| 7,442,171 | B2 | 10/2008 | Stephens et al. | |
| 7,517,321 | B2 | 4/2009 | McCullough et al. | |
| 7,854,706 | B2 | 12/2010 | Hibner | |
| 7,938,786 | B2 | 5/2011 | Ritchie et al. | |
| 8,118,755 | B2 | 2/2012 | Hibner et al. | |
| 8,206,316 | B2 | 6/2012 | Hibner et al. | |
| 8,277,394 | B2 | 10/2012 | Hibner | |
| 8,282,754 | B2 | 10/2012 | Coonahan et al. | |
| 8,485,989 | B2 | 7/2013 | Videbaek | |
| 11,013,499 | B2 | 5/2021 | Shabaz | |
| 2005/0203439 | A1 * | 9/2005 | Heske | A61M 39/1055 606/167 |
| 2011/0087131 | A1 * | 4/2011 | Videbaek | A61B 10/0275 600/567 |
| 2011/0208090 | A1 * | 8/2011 | Parihar | A61B 10/0275 600/568 |
| 2014/0039343 | A1 * | 2/2014 | Mescher | A61B 90/98 600/562 |
| 2018/0092633 | A1 * | 4/2018 | Peliks | A61B 10/0266 |
| 2019/0231325 | A1 | 8/2019 | Nock | |
| 2019/0321009 | A1 | 10/2019 | Nevo et al. | |
| 2021/0153850 | A1 | 5/2021 | Kjeldsen et al. | |

FOREIGN PATENT DOCUMENTS

| | | | | |
|---|---|---|---|---|
| WO | WO 2014/028366 | | 2/2014 | |
| WO | WO-2018098239 | A1 * | 5/2018 | A61B 10/0283 |

* cited by examiner

USER INTERFACE FOR BIOPSY DEVICE

PRIORITY

This application is a continuation of International Application Number PCT/US2020/057466, filed on Oct. 27, 2020, which claims priority to U.S. Provisional Application Ser. No. 62/926,805 entitled "User Interface for Biopsy Device," filed on Oct. 28, 2019, the disclosures of which are incorporated by reference herein.

BACKGROUND

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

One technique for collecting a breast biopsy is to use a core needle biopsy device. Core needle biopsy devices may use a sharp, solid piercer equipped with a lateral tissue receiving notch positioned adjacent to the distal end of the piercer. When tissue is received within the notch, an elongate hollow cutting sheath is translated over the notch to sever a tissue sample. The severed tissue sample is then stored within the notch until both the piercer and the cutting sheath are removed from the patient. Thus, in core-needle biopsy devices, only one tissue sample can be collected per insertion of the piercer and cutting sheath.

Another technique for conducting a breast biopsy is to conduct a breast biopsy using a vacuum-assisted breast biopsy device. In contrast to core needle breast biopsy procedures, vacuum-assisted breast biopsy devices permit the probe to remove multiple samples without requiring the probe be removed from the breast after every sample is collected. For instance, in a vacuum assisted breast biopsy device, a hollow needle is used to penetrate tissue. The hollow needle includes a lateral aperture adjacent to a sharp distal tip. A hollow cutter is disposed within the hollow needle and is moved axially relative to the lateral aperture of the needle to sever tissue samples. Once a tissue sample is severed by the hollow cutter, the tissue sample is transported axially though the cutter and collected in a tissue collection feature.

Examples of vacuum assisted biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 1, 2012; and U.S. Pat. No. 8,206,316, entitled "Tetherless Biopsy Device with Reusable Portion," issued on Jun. 26, 2012. The disclosure of each of the above-cited U.S. Patents is incorporated by reference herein.

Examples of core needle biopsy devices are disclosed in U.S. Pat. No. 5,560,373, entitled "Needle Core Biopsy Instrument with Durable or Disposable Cannula Assembly," issued on Oct. 1, 1996; U.S. Pat. No. 5,817,033, entitled "Needle Core Biopsy Device," issued on Oct. 6, 1998; and U.S. Pat. No. 5,511,556, entitled "Needle Core Biopsy Instrument," issued on Apr. 30, 1996. The disclosure of each of the above-cited U.S. Patents is incorporated by reference herein.

A challenge in both biopsy device configurations described above is operating the biopsy device with real-time feedback and limited user interaction points. Such challenges can arise due to the unique piercer and cutter configuration that is encountered in the context of core needle biopsy devices. For instance, due to the relatively simple nature of core needle biopsy devices, the piercer and/or cutting sheath can be driven by a spring actuated mechanism. However, such mechanisms can require multiple buttons or user input features to engage different movements during a tissue acquisition sequence. The multiplicity of user input features can be undesirable in some examples due to operator confusion. In addition, such mechanisms provide limited means for operator feedback, thereby compounding operator confusion. Thus, certain user interface features may be desirable for integration into a biopsy device that simplify the operator experience while also providing real-time feedback.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
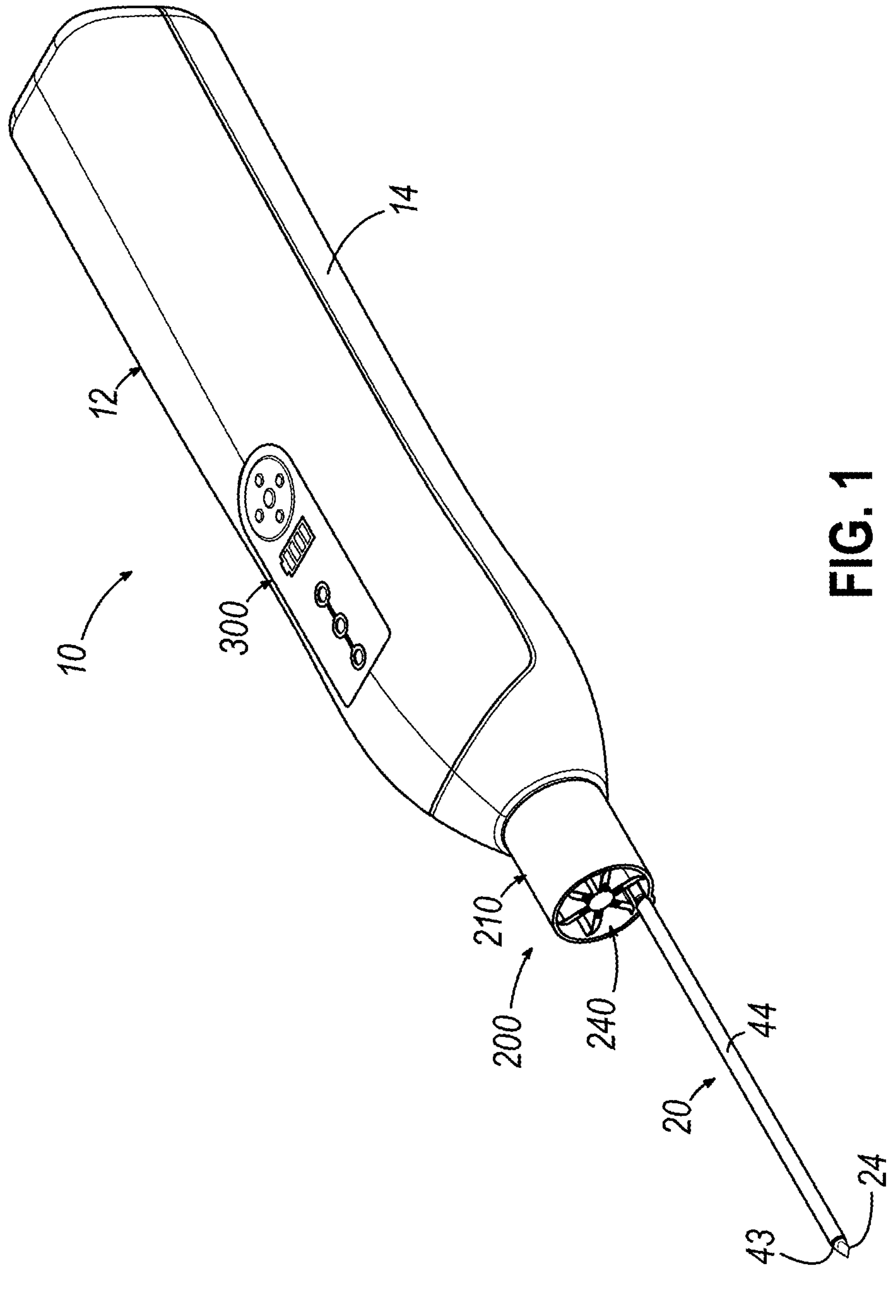
FIG. 1 depicts a perspective view of an exemplary core needle biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Biopsy devices may be used to collect tissue samples in a variety of ways. For example, in some instances tissue samples are collected into a single tissue basket such that all tissue samples collected during a given biopsy procedure are deposited into the single tissue sample basket. In some other instances, tissue samples are collected into a tissue sample holder having separate compartments for each collected tissue sample. Such a multi-compartment tissue sample holder may additionally include trays or strips that individually hold each tissue sample separately from the other tissue samples. Such trays or strips may be removable or otherwise separable from the tissue sample holder at the conclusion of a biopsy procedure.

Regardless of the structure in which the tissue samples are stored, tissue samples may be collected using biopsy devices under the guidance of various imaging modalities such as ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used.

Vacuum assisted biopsy devices and core needle biopsy devices both may have various advantages over the other, depending on context. For instance, one advantage of vacuum assisted biopsy devices is that vacuum assistance permits removal of multiple tissue samples using a single insertion. However, while core needle biopsy devices lack this feature, use of core needle biopsy devices may still be desirable. For instance, core needle biopsy devices are generally capable of having smaller needles relative to core needle biopsy devices, thereby reducing patient anxiety and increasing the capacity of the needle to penetrate a lesion. Therefore, in some instances it may be desirable to incorporate the feature of multiple sample removal of a vacuum assisted biopsy device into a core needle biopsy device to achieve the benefits present in both styles of biopsy device.

A desirable feature of the device described herein, which is a core needle biopsy device, is that the device allows for single insertion with multiple samples being obtained whilst using a core needle type device. To facilitate this functionality, the biopsy device further includes a tissue sample holder having one or more features to facilitate collection of a severed tissue sample from a notch, dugout, aperture, and/or other sample collection feature.

I. EXEMPLARY CORE NEEDLE BIOPSY DEVICE WITH MULTI-SAMPLE COLLECTION

FIG. 1 shows an exemplary core needle biopsy device (10) for use in a breast biopsy procedure. Core needle biopsy device (10) of the present example comprises a body (12) and a needle assembly (20) extending distally from body (12). Body (12) includes an outer housing (14) and a user interface (300) disposed on outer housing (14). As will be described in greater detail below, outer housing (14) encloses various components of biopsy device (10). As will also be described in greater detail below, such components can be activated or otherwise controlled by user interface (300) to drive needle assembly (20) through a cutting cycle and a tissue acquisition cycle. To this end, outer housing (14) of the present example is sized and shaped for grasping by an operator using a single hand. Similarly, user interface (300) is positioned for actuation by a single hand. Although not shown, it should be understood that in some examples outer housing (14) may comprise multiple parts such that each part interconnects to form outer housing (14). For instance, in some examples outer housing (14) can be formed by the combination of a disposable probe and a reusable holster.

A. Exemplary Needle Assembly

Figure 2:
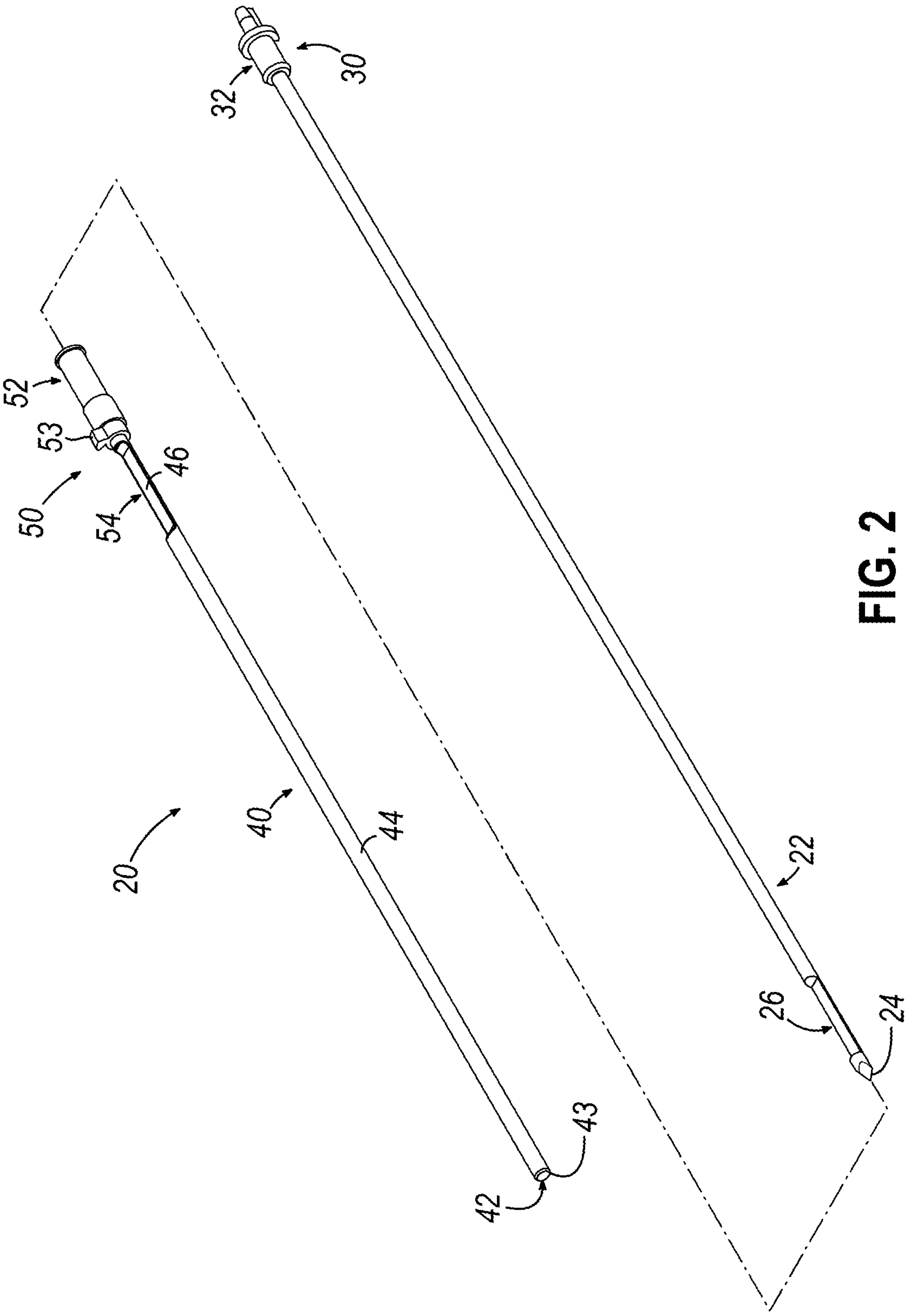
FIG. 2 depicts an exploded view of a needle assembly of the core needle biopsy device of FIG. 1.
Figure 3:
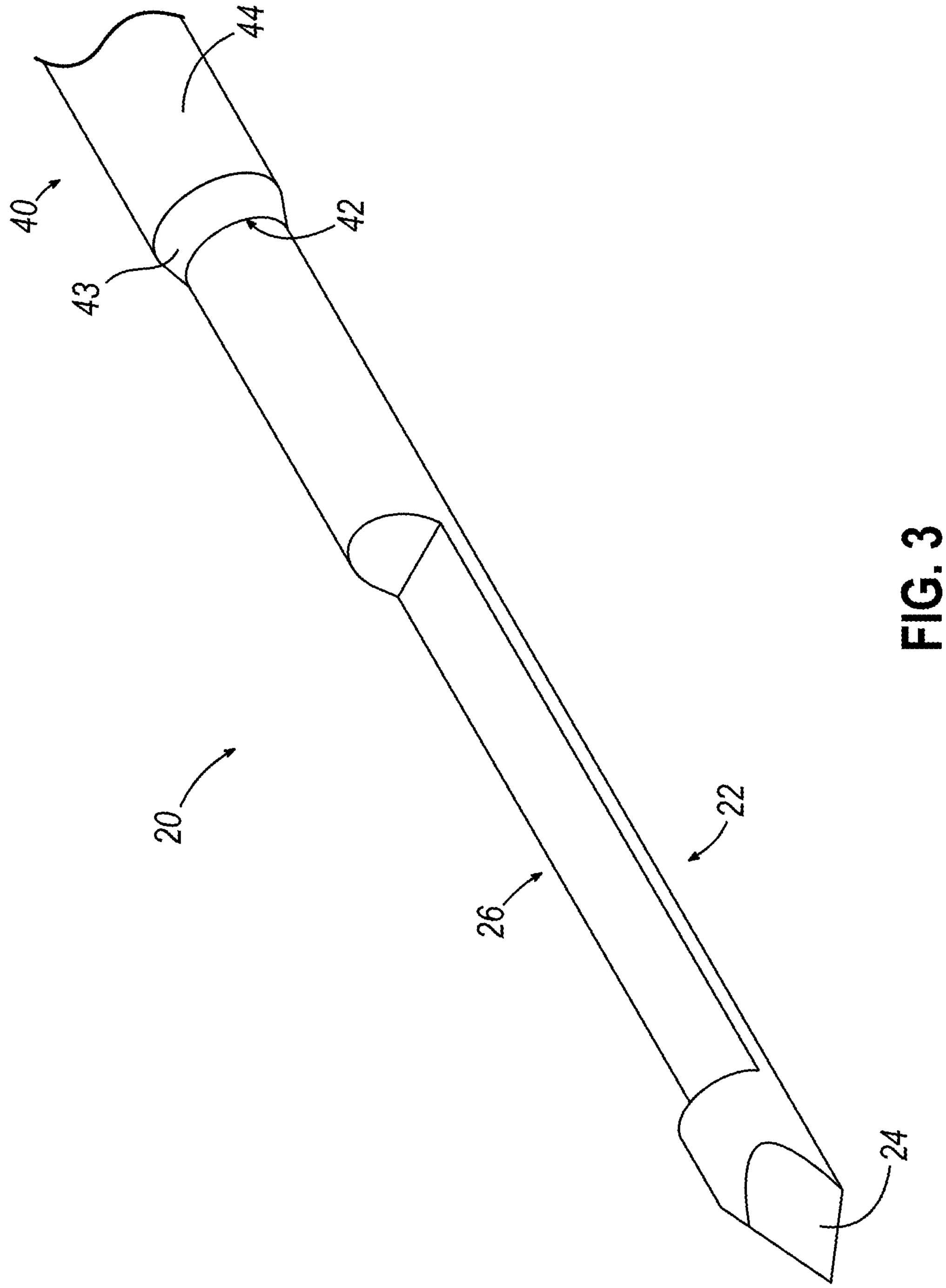
FIG. 3 depicts a perspective view of the distal portion of the needle assembly of FIG. 2.

FIGS. 2 and 3 show needle assembly (20) in greater detail. As can be seen in FIG. 2, needle assembly (20) comprises an elongate piercer (22) and an elongate cutter (40). As will be described in greater detail below, piercer (22) is generally movable relative to cutter (40) to pierce tissue and collect tissue samples, while cutter (40) is generally movable relative to piercer (22) to sever tissue samples. Piercer (22) comprises a generally cylindrical rod having a sharp distal tip (24) and a notch (26) disposed adjacent to distal tip (24). As will be described in greater detail below, distal tip (24) is generally configured to penetrate tissue of a patient. As will also be described in greater detail below, notch (26) is generally configured to receive tissue therein such that a tissue sample may be collected within notch (26) after the tissue sample is severed by cutter (40).

An end portion (30) is disposed on the proximal end of piercer (22). End portion (30) of the present example is overmolded onto the proximal end of piercer (22) and is generally configured to enhance the manipulability of piercer (22). In particular, end portion (30) comprises a receiving feature (32) in the form of a cylindrical indentation or notch. Receiving feature (32) is configured to receive a portion of a piercer drive assembly (300). As will be described in greater detail below, this permits piercer drive assembly (300) to drive movement of piercer (22) through a predetermined sequence of movement.

Cutter (40) comprises a generally hollow cylindrical tube that is configured to receive piercer (22) therein. Cutter (40) comprises an open distal end (42), a cannula portion (44) and an end portion (50). Open distal end (42) is configured to permit at least a portion of piercer (22) to protrude from cutter (40) when piercer (22) is moved relative to cutter (40). As will be described in greater detail below, this configuration permits needle assembly (20) to move through the cutting cycle and the tissue acquisition cycle by permitting notch (26) of piercer (22) to move relative to distal end (42) of cutter (40).

Open distal end (42) of the present example includes a tapered edge (43). Tapered edge (43) is generally configured to slice through tissue to separate tissue samples when cutter (40) is moved relative to notch (26) of piercer (22). Thus, it should be understood that tapered edge (43) is generally configured to act as a blade. Although the present example is described and shown as using a tapered configuration, it should be understood that in other examples various alternative configurations can be used. For instance, in some examples tapered edge (43) includes a plurality of serrations in addition or in alternative to the taper shown. In still other examples, tapered edge (43) can include any other additional or alternative cutting surface as will be apparent to those of ordinary skill in the art in view of the teachings herein.

Cannula portion (44) of cutter (40) extends proximally from distal end (42) through end portion (50) such that piercer (22) can be received with the proximal end of cutter (40). Unlike end portion (30) of piercer (22), end portion (50) of cutter (40) is generally elongate such that end portion (50) can accommodate additional features that will be described in greater detail below. In the present example, the distal extension of end portion (50) can be relative to outer housing (14) to permit a portion of end portion (50) to be accessible to an operator for tissue sample collection purposes. A merely illustrative example of a tissue collection mechanism associated with end portion (50) will be described in greater detail below.

End portion (50) of cutter (40) comprises a receiving feature (52) and a tissue collection feature (54). As with receiving feature (32) of piercer (22), receiving feature (52) of end portion (50) comprises a cylindrical indentation, slot, or other receiving feature that is configured to receive at least a portion of a cutter drive assembly (200). As will be described in greater detail below, receiving feature (52) is configured to receive at least a portion of cutter drive assembly (200) to permit cutter drive assembly (200) to move cutter (40) through a predetermined sequence of movement.

Tissue collection feature (54) is disposed distally relative to receiving feature (52). Tissue collection feature (54) generally defines an elongate notch that is open to cannula portion (44) of cutter (40). Thus, cannula portion (44) includes a cutout portion (46) that is adjacent to, or otherwise defines, tissue collection feature (54). Accordingly, it should be understood that tissue collection feature (54) is in communication with the hollow interior, or a lumen, defined by cannula portion (44). As will be described in greater detail below, this relationship between tissue collection feature (54) and cannula portion (44) permits an operator to remove tissue samples from cutter (40) as they are collected by piercer (22).

End portion (50) further includes a driver (53) extending outwardly from an outer surface of end portion (50). Driver (53) generally comprises a square or rectangular shape. As will be described in greater detail below, driver (53) is generally configured to manipulate certain features associated with various tissue collection features described herein. Although driver (53) of the present example is shown in connection with end portion (50), it should be understood that in other examples driver (53) can be associated with other components or omitted entirely.

FIG. 3 shows piercer (22) disposed within cutter (40). As can be seen, cutter (40) is generally configured to receive piercer (22) such that piercer (22) is coaxial with cutter (40). In addition, piercer (22) is generally movable relative to open distal end (42) of cutter (40). It should be understood that in some circumstances piercer (22) moves relative to cutter (40), while cutter (40) remains stationary. In other circumstances, cutter (40) moves relative to piercer (22), while piercer (22) remains stationary. In either case, it should be understood that piercer (22) and cutter (40) are generally configured such that notch (26) of piercer (22) moves into and out of cutter (40) such that notch (26) can be disposed distally or proximally relative to open distal end (42) of cutter (40). As will be described in greater detail below, this configuration permits piercer (22) and cutter (40) to cooperate to pierce tissue, cut a tissue sample, and retract the tissue sample for collection by an operator via tissue collection feature (54).

B. Exemplary Drive Assembly

Figure 4:
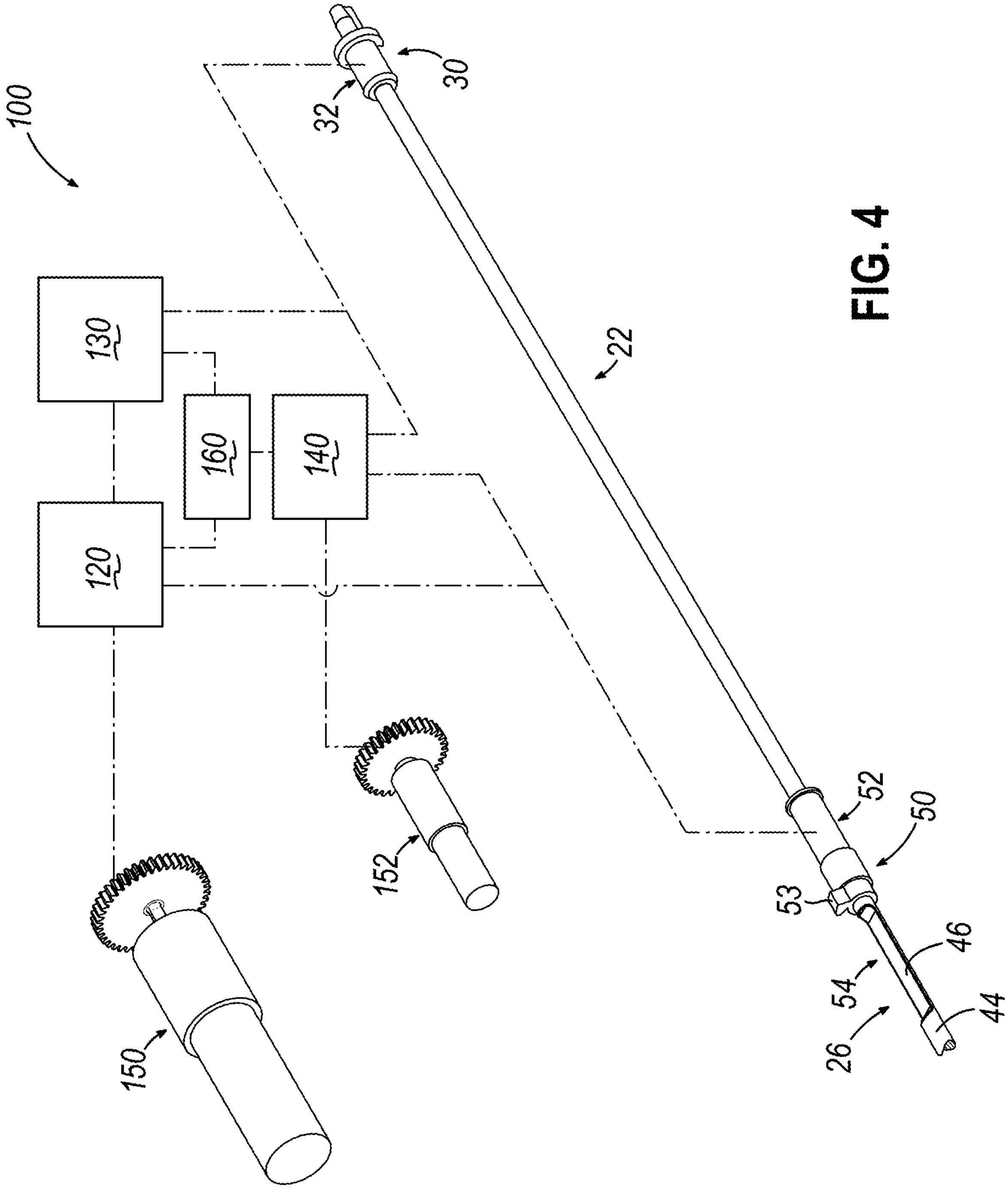
FIG. 4 depicts a perspective view of a drive assembly of the core needle biopsy device of FIG. 1.

FIG. 4 shows the internal components of body (12) of biopsy device (10) with outer housing (14) removed. As can be seen, inside outer housing (14), body (12) includes a drive assembly (100). Drive assembly (100) is generally configured to engage needle assembly (20) to drive piercer (22) and cutter (40) through a predetermined sequence of movements to thereby pierce tissue and acquire a plurality of tissue samples with a single insertion of needle assembly (20) into a patient. Although not shown, it should be understood that outer housing (14) defines various internal geometries that support or otherwise engage drive assembly (100). As will be understood, such internal geometries are used to provide relative movement of various components of drive assembly (100) relative to other components of drive assembly (100) and/or outer housing (14).

Drive assembly (100) comprises a cutter drive assembly (120), a piercer drive assembly (130), and a firing assembly (140). Generally, firing assembly (140) is configured to cock (or arm) and fire cutter (40) and piercer (22) in a predetermined sequence to sever a tissue sample. To collect the severed tissue sample, cutter drive assembly (120) is generally configured to retract cutter (40). Similarly, piercer drive assembly (130) is generally configured to retract piercer (22). It should be understood that, in some examples, both cutter drive assembly (120) and piercer drive assembly (130) can be configured to rotate cutter (40) and/or piercer (22), respectively.

Firing assembly (140) is generally shown schematically in the present example. Thus, it should be understood that in some examples firing assembly (140) can take on a variety of forms having a combination of gears, racks, leadscrews, carriages, springs, and/or etc. Such components of firing assembly (140) can generally be configured to rapidly fire cutter (40) and piercer (22) in a predetermined sequence to penetrate tissue. For instance, in some examples, firing assembly (140) is configured to rapidly fire piercer (22) distally to penetrate tissue. Firing assembly (140) is also configured to rapidly fire cutter (40) distally. The firing of cutter (40) can be either delayed relative to piercer (22) or slower relative to piercer (22) such that notch (26) can be exposed relative to cutter (40). This sequence can permit tissue to enter notch (26), so that it can be severed by subsequent movement of cutter (40). In addition, it should be understood that firing assembly (140) can include other components and/or features to permit cocking of cutter (40) and/or piercer (22) prior to firing.

Cutter drive assembly (120) is generally configured to translate and/or rotate cutter (40) either independently of piercer (22) or in concert therewith. For instance, cutter drive assembly (120) can include various combinations of gears, racks, leadscrews, carriages, springs, and/or etc. to drive cutter (40) through a predetermined sequence. In one such sequence, cutter (40) is retracted proximally relative to outer housing (14) to prepare cutter (40) for a tissue collection sequence that will be described in additional detail below. In addition, cutter drive assembly (120) can also be configured to rotate cutter (40) in a predetermined sequence to assist with the tissue collection sequence described in greater detail below.

Piercer drive assembly (130) is generally configured to translate and/or rotate piercer (22) either independently of cutter (40) or in concert therewith. For instance, piercer drive assembly (120) can include various combinations of gears, racks, leadscrews, carriages, springs, and/or etc. to drive piercer (22) through a predetermined sequence. In one such sequence, piercer (22) is retracted proximally relative to cutter (40) after severing a tissue sample to retract the tissue sample proximally towards outer housing (14). Once piercer (22) is retracted, the tissue sample can be extracted for collection in the tissue collection sequence described in greater detail below.

In the present example, drive assembly (100) is powered by one or more motors (150, 152). In particular, drive assembly (100) of the present example includes a drive motor (150) and a firing motor (152). Drive motor (150) of the present example is in communication with both cutter drive assembly (120) and piercer drive assembly (130) to provide rotational motion to both assemblies, which ultimately drives translation and/or rotation of both cutter (40) and piercer (22). Similarly, firing motor (152) is in communication with firing assembly (140) to drive firing and/or cocking of cutter (40) and piercer (22). Although drive assembly (100) of the present example includes two motors (150, 152), it should be understood that in other examples any suitable number of motors may be used such as a single motor, or three or more motors. In addition, motors (150, 152) can be configured to drive cutter drive assembly (120), piercer drive assembly (130), and/or firing assembly (140) in various combinations.

Although cutter drive assembly (120), piercer drive assembly (130), and firing assembly (140) of the present example are shown schematically as three separate drive assemblies, it should be understood that in other examples various elements of cutter drive assembly (120), piercer drive assembly (130), and firing assembly (140) can be combined into a single drive assembly or multiple drive assemblies to drive motion of cutter (40) and piercer (22) in accordance with the sequences described herein. In some examples, cutter drive assembly (120), piercer drive assembly (130), and firing assembly (140) can be constructed in accordance with at least some of the teachings of US Ser. No. 16/381,573, entitled "Core Needle Biopsy Device for Collecting Multiple Samples in a Single Insertion," filed on Apr. 11, 2019, the disclosure of which is incorporated by reference herein.

C. Exemplary Tissue Sample Holder

Figure 5:
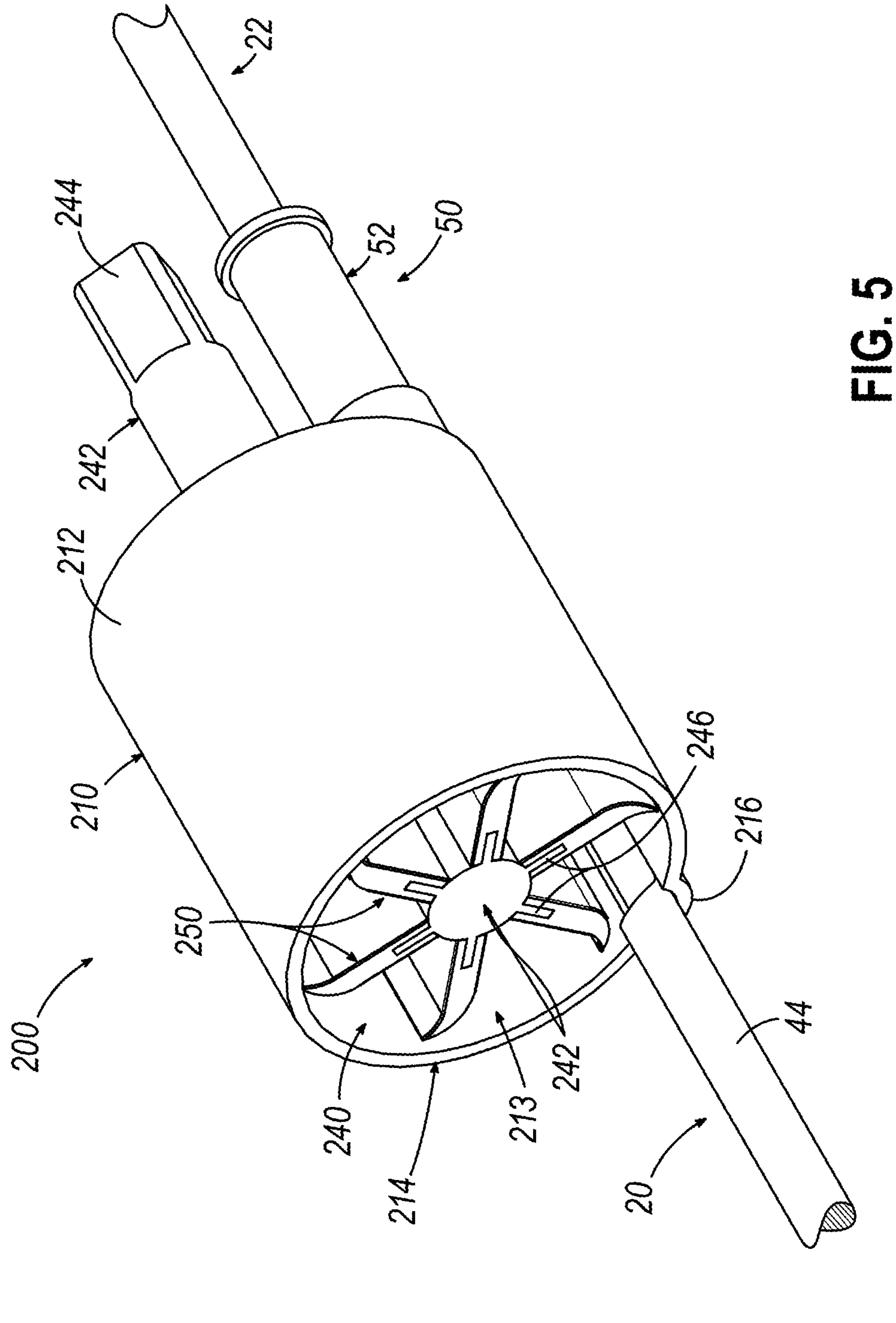
FIG. 5 depicts a perspective view of a tissue sample holder of the core needle biopsy device of FIG. 1.

As shown in FIG. 5, biopsy device (10) of the present example includes a tissue sample holder (200) for the collection of multiple samples during a single insertion of needle assembly (20). Tissue sample holder (200) of the present example includes an extraction mechanism (240) disposed within a cylindrical outer housing (210). Tissue sample holder (200) is generally configured to collect a plurality of tissue samples from tissue collection feature (54) of needle assembly (20) during a biopsy procedure using rotation of extraction mechanism (240). As will be described in greater detail below, tissue sample holder (200) is generally configured to collect and store six tissue samples, although any suitable number can be collected and stored in other examples.

Outer housing (210) includes a cylindrical body (212) defining a sample chamber (213) and an open distal end (214), a closed proximal end (not shown), and a needle receiving portion (216) extending between open distal end (214) and the closed proximal end. In the present example, outer housing (210) is generally transparent to promote visibility of tissue samples during sample collection. Although outer housing (210) of the present example is shown as having open distal end (214), it should be understood that in other examples, open distal end (214) can be closed or capped to seal sample chamber (213) of outer housing (210) relative to the environment.

Needle receiving portion (216) is generally configured as a semi-cylindrical indentation or bulge in the otherwise cylindrical shape of outer housing (210). Needle receiving portion (216) is generally sized to correspond to the size and shape of needle assembly (20). Thus, needle receiving portion (216) generally defines a pocket or recessed area where needle assembly (20) can rest.

Extraction mechanism (240) includes a shaft (242) and a plurality of wipers (250) arranged around shaft (242). Shaft (242) is generally rotatable to thereby rotate wipers (250) within outer housing (210) to collect and store tissue samples as each tissue sample is collected by needle assembly (20). The proximal end of shaft (242) includes a keyed portion (244) that is configured to communicate with either a manual or motorized driver to rotate shaft (242).

The distal end of shaft (242) includes a plurality of couplers (246) extending outwardly from an exterior surface of shaft (242). Each coupler (246) is generally configured to receive a corresponding wiper (250) to provide a secure base for each wiper (250) to fasten to. Each coupler (246) of the present example defines a generally rectangular cross-section. In other examples, various alternative cross-sectional shapes can be used such as triangular, circular, square, or the like. Although not shown, it should be understood that couplers (246) can extend axially along the length of shaft (242) for a length approximately equivalent to the length of each wiper (250).

Each wiper (250) defines a generally curved or wave-shaped surface on the outer end. In the present curved shape, there is a concavity that is oriented in the direction of rotation of shaft (242). The particular shape of each wiper (250) is generally configured to atraumatically engage a tissue sample to manipulate the tissue sample out of tissue collection feature (54) and into sample chamber (213) of outer housing (210). Although each wiper (250) of the present example has a curved shape, it should be understood that in other examples various other shapes can be used such as rounded, square, triangular, and/or etc. In addition, although each wiper (250) is shown as having a generally consistent shape longitudinally, it should be understood that in some examples, the shape can be varied as wiper (250) extends axially.

Wipers (250) are generally formed of a flexible yet partially resilient material such as rubber or elastomer. For instance, wipers (250) are generally flexible enough to flex around the interface between outer housing (210) and needle assembly (20). This flexibility can be generally desirable to reduce trauma when each wiper (250) engages tissue, while also promoting complete engagement between each wiper (250) and tissue. Meanwhile, at least some resiliency is provided so that each wiper (250) can push or otherwise move a tissue sample. In some examples, the flexibility of each wiper (250) can be characterized in terms of a durometer. Although several suitable durometers can be used, one suitable durometer range is 30 to 80.

Each coupler (246) and wiper (250) is generally arranged around shaft (242) in an angularly spaced manner such that wipers (250) are spaced equal angular distances from each other. This generally results in couplers (246) and wipers (250) collectively forming a starburst pattern. This configuration may be desirable to divide sample chamber (213) into six equal segments for the storage of tissue samples. However, it should be understood that in other examples, other suitable spacing can be used including unequal spacing.

Although not shown, it should be understood that tissue sample holder (200) can have multiple different configurations for the collection of one or more tissue samples. By way of example only, in some examples, tissue sample holster (200) can be configured in accordance with any one or more of the teachings of U.S. Ser. No. 62/916,277, entitled "Sample Management for Core Needle Biopsy Device," filed on Oct. 17, 2019, the disclosure of which is incorporated by reference herein.

In use, collection of a tissue sample using tissue sample holder (200) can begin after cutter (40) and piercer (22) have been driven by drive assembly (100) to sever and collect a tissue sample. In particular, once the tissue sample has been severed, the tissue sample is transported to tissue collection feature (54) using notch (26) of piercer (22).

In the present example, tissue sample holder (200) is positioned along the axis of needle assembly (20) such that each wiper (250) is aligned with tissue collection feature (54). Accordingly, to collect the tissue sample, shaft (242) can be rotated to rotate each wiper (250) within sample chamber (213) to sweep a selected wiper (250) adjacent to tissue collection feature (54) across notch (26). As the selected wiper (250) sweeps across notch (26), the selected wiper (250) engages the tissue sample to push the tissue sample out of tissue collection feature (54).

Once the selected wiper (250) sweeps across notch (26), rotation of shaft can continue. Continued rotation results in the tissue sample being moved around the interior of outer housing (210) to permit the tissue sample to be stored and ready needle assembly (20) for collection of further tissue samples. At this stage, rotation of shaft (242) can continue in coordination with sequential movement of cutter (40) and piercer (22) for the severing and collection of another tissue sample. Alternatively, rotation of shaft (242) can temporarily cease to permit cutter (40) and piercer (22) to reposition and collect another tissue sample. Regardless, once another tissue sample is collected, rotation of shaft (242) can be used to sweep another wiper (250) across notch (26) to collect another tissue sample. The same process can then be repeated any suitable number of times until tissue sample holder (200) is full or a desired number of tissue samples have been collected.

II. EXEMPLARY USER INTERFACE

In some examples, it may be desirable to incorporate certain user interface features into biopsy device (10) that provide an operator with real-time feedback and simplified interaction. For instance, as described above, drive assembly (100) and firing assembly (140) are configured to drive needle assembly (20) in a predetermined sequence of movements to collect one or more tissue samples. In some examples, this sequence of movements can be controlled at various points during the sequence. However, such control can may lead to the addition of multiple buttons or other operator input features. In some examples, this configuration may be undesirable because multiple operator input features could lead to operator confusion. Thus, it may be desirable to limit the particular number of operator input features, while still providing some control. In addition, the predetermined sequence described above can also lead to operator confusion due to limited operator feedback during the sequence of movements. Thus, it may be desirable in some examples to include various indicators to provide real-time feedback related to the status of biopsy device (10). Although an exemplary user interface (300) is described below, it should be understood that various alternative user interfaces may be used without departing from the teachings included herein.

Figure 6:
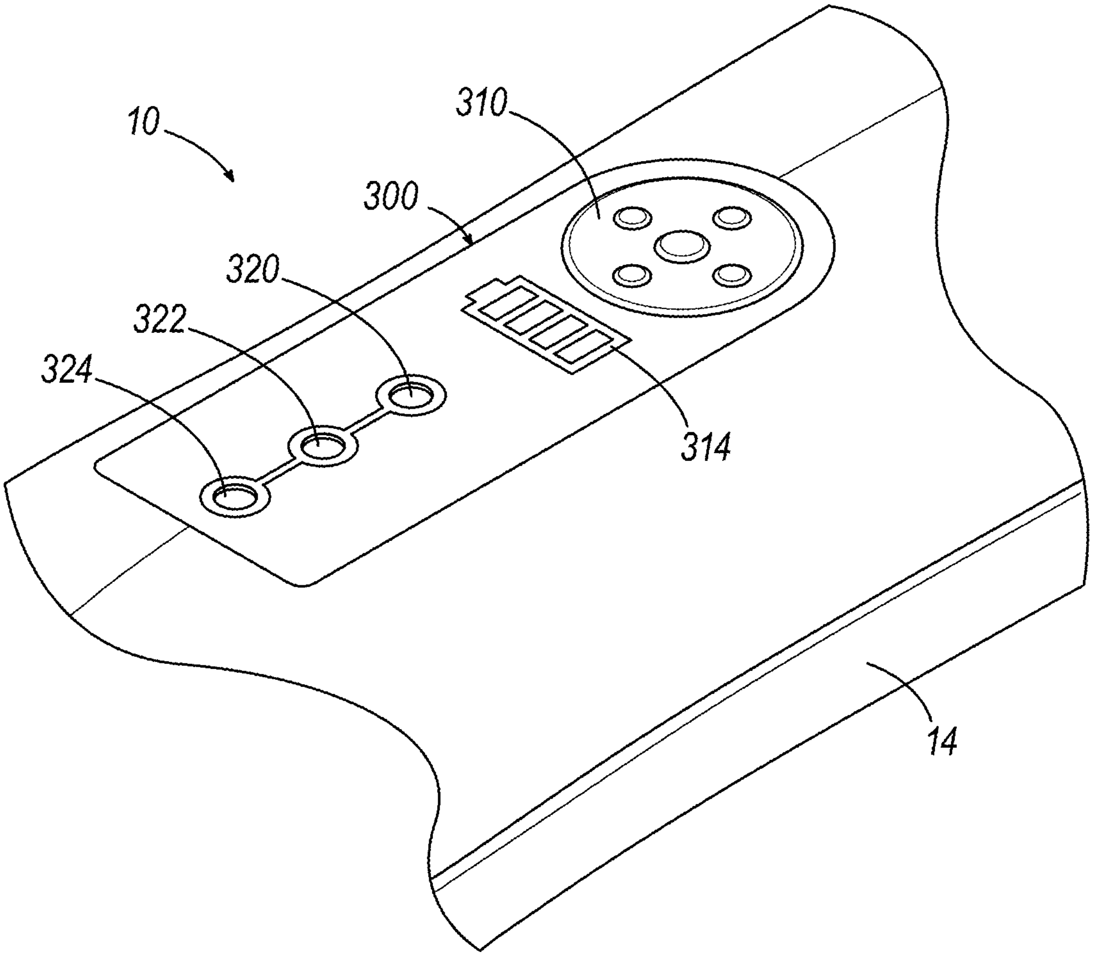
FIG. 6 depicts a detailed perspective view of an exemplary user interface of the core needle biopsy device of FIG. 1.

FIG. 6 shows an exemplary user interface (300) that can be readily incorporated into biopsy device (10) described above. User interface (300) of the present example is generally configured to control operation of drive assembly (100) and firing assembly (140) to collect one or more tissue samples using needle assembly (20). In addition, user interface (300) is generally configured to provide real-time feedback to an operator as to the status of biopsy device (10) as drive assembly (100) and firing assembly (140) move needle assembly (20) through various operational states.

User interface (300) includes a button or actuator (310), a power indicator (314), and a series of indicators (320, 322, 324) related to the operational status of biopsy device (10). Actuator (310) of the present example is in communication with drive assembly (100) and/or firing assembly (140) either by direct electrical communication, direct mechanical communication, or some combination thereof. Alternatively, in some examples, actuator (310) is in communication with a controller or other electronic circuitry configured to communicate with drive assembly (100) and/or firing assembly (140). Regardless, it should be understood that actuator (310) is generally configured to control the operation of drive assembly (100) and/or firing assembly (140). As will be described in greater detail below, this generally can involve an operator pressing or otherwise manipulating actuator (310) to cause drive assembly (100) and/or firing assembly (140) to move needle assembly (20) through various predetermined operational sequences.

Power indicator (314) is positioned distally of actuator (310) and is generally configured to provide an indication of the power status of biopsy device (10). In particular, power indicator (314) of the present example comprises a row of a plurality of light emitting diodes (LED) configured illuminate in a predetermined sequence. Biopsy device (10) of the present example is battery (160) operated. Thus, the sequential illumination of the LEDs of power indicator (314) is configured to provide an indication of the power remaining within battery (160). Although power indicator (314) of the present example includes four LED's, it should be understood that in other examples any suitable number of LED's can be used.

The series of indicators (320, 322, 324) includes a proximal indicator (320), an intermediate indicator (322), and a distal indicator (324). Generally, each indicator (320, 322, 324) is configured to independently transition through a plurality of states to communicate certain status information related to biopsy device (10). For instance, in the present example, each indicator (320, 322, 324) is an LED configured to transition between an off state (not emitting light), a solid on state (emitting light), and a blinking on state (periodically emitting light). However, it should be understood that in other examples the particular states used can be varied. For instance, in some examples, indicators (320, 322, 324) are configured to emit a variety of different colors and such colors can be used to communicate certain status information related to biopsy device (10). In other examples, illumination of indicators (320, 322, 324) can be controlled to blink each indicator (320, 322, 324) at a variable rate to communicate certain status information related to biopsy device (10). Of course, various alterative states may be used as will be apparent to those of ordinary skill in the art in view of the teachings herein.

As noted above, indicators (320, 322, 324) are configured as three separate LEDs. However, it should be understood should be understood that in other examples various alternative configurations can be used. For instance, in some examples, indicators (320, 322, 324) can be formed by a single LED screen graphically divided into a plurality of segments. Such segments can then be illuminated similar to the illumination described above. Alternatively, the illumination described above can be replaced with symbols, graphics, numbers, emojis, and/or etc. to provide the same status information through alternative means.

FIGS. 7-15 show an exemplary sequence of operation that can be used to communicate the operational status of biopsy device (10) to an operator via indicators (320, 322, 324). In an initial state, outer housing (14) is divided such that a probe is separated from holster. To begin the sequence the probe is attached to the holster as indicated in block (400) to completely form outer housing (14). Once probe is attached to holster as indicated in block (400), an initialization sequence begins automatically as indicated by block (410). As biopsy device (10) progresses through the initialization sequence, proximal indicator (320), intermediate indicator (322), and distal indicator (324) all flash or blink in unison as shown in block (412) to communicate that biopsy device (10) is progressing through the initialization sequence. The status of each indicator (320, 322, 324) as shown in block (412) is shown graphically in FIG. 8.

Once initialization has completed, biopsy device (10) stops automatically. Meanwhile, proximal indicator (320), intermediate indicator (322), and distal indicator (324) all switch from flashing or blinking to continuously illuminating light or otherwise being solidly highlighted. This state of indicators (320, 322, 324) is shown schematically in block (422) of FIG. 7 and graphically in FIG. 9.

Figure 7:
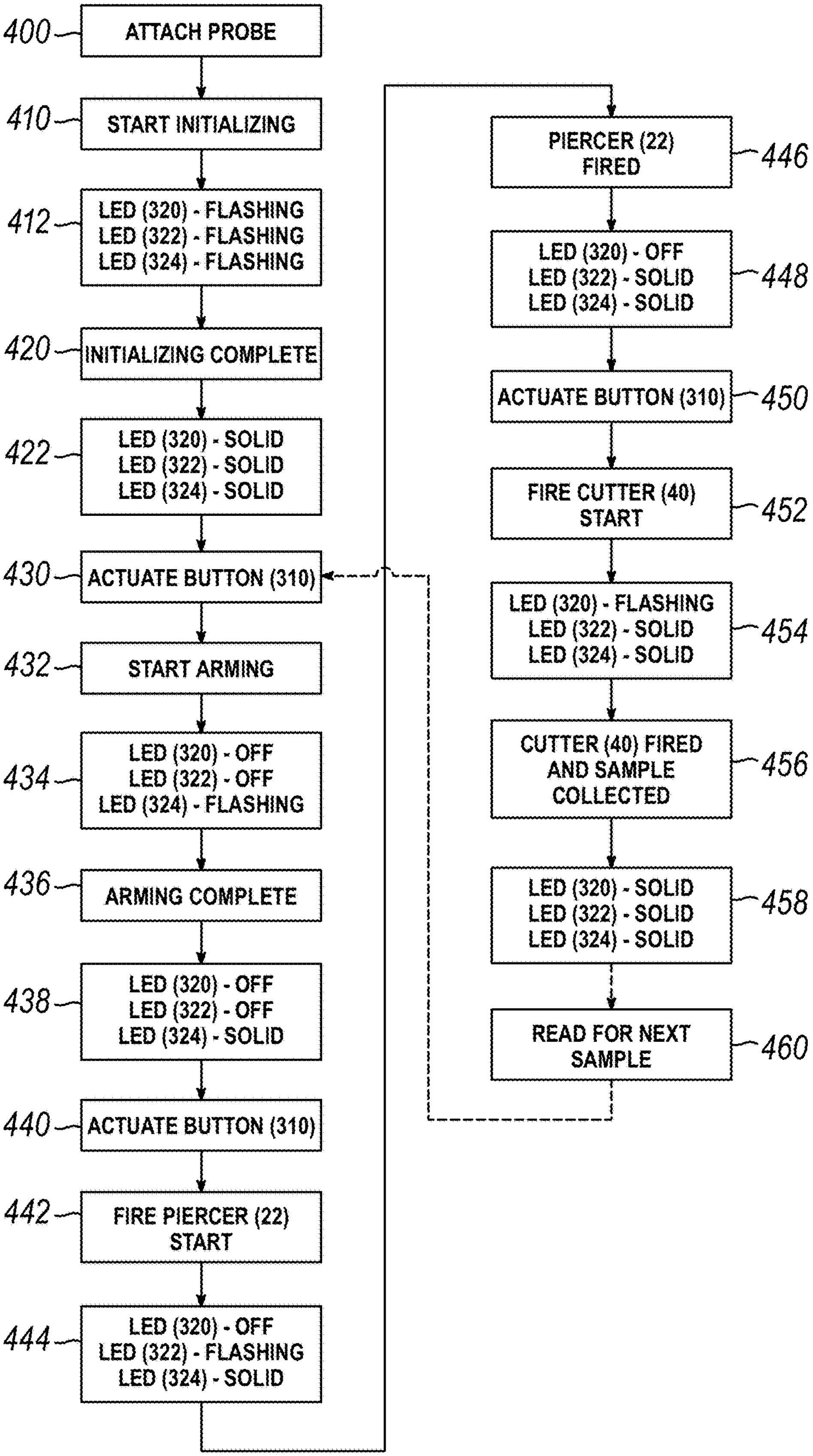
FIG. 7 depicts a schematic flow chart of a use of the core needle biopsy device of FIG. 1, with various states of the user interface of FIG. 6.
Figure 8:
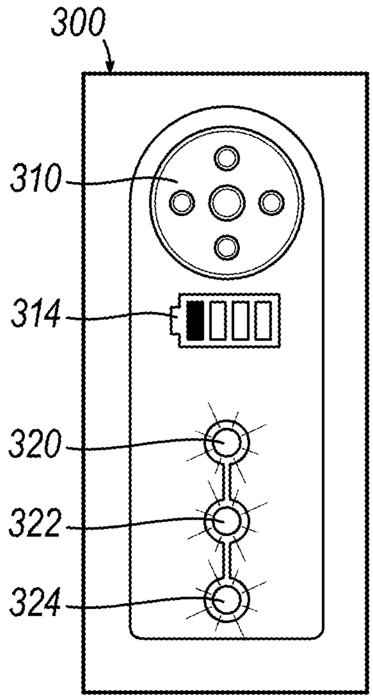
FIG. 8 depicts a detailed top plan view of the user interface of FIG. 6, in a first state.
Figure 9:
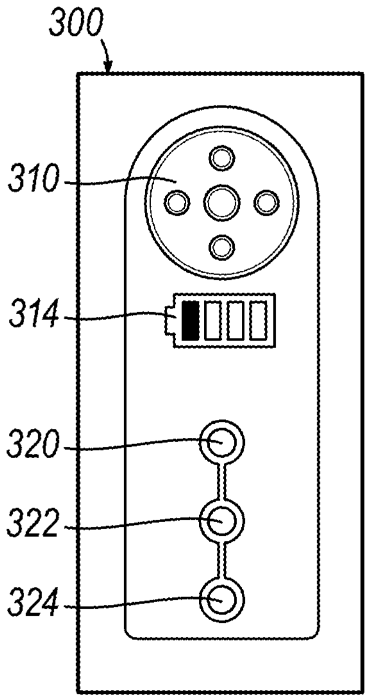
FIG. 9 depicts another detailed top plan view of the user interface of FIG. 6, in a second state.

When indicators are all continuously illuminated (320, 322, 324) as shown schematically in block (422) of FIG. 7 and graphically in FIG. 9, an operator may understand that initialization has completed. At this stage, an operator can press or otherwise actuate actuator (310) to begin arming needle assembly (20). After actuator (310) is pressed, drive assembly (100) and/or firing assembly (140) can be activated to automatically arm or cock both piercer (22) and cutter (40). During this sequence, distal indicator (320) and intermediate indicator (322) can be switched to an off state as shown in block (434) of FIG. 7. Meanwhile, proximal indicator (324) can be switched to a flashing or blinking state as also shown in block (434) of FIG. 7. The combination of indicators (320, 322, 324) as shown schematically in block (434) of FIG. 7 and graphically in FIG. 10 can communicate that arming of biopsy device (10) is in progress.

Figure 10:
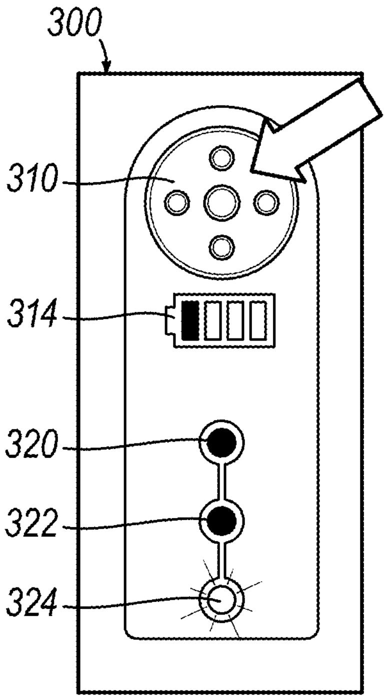
FIG. 10 depicts still another detailed top plan view of the user interface of FIG. 6, in a third state.

The state of indicators (320, 322, 324) as shown schematically in block (434) of FIG. 7 and graphically in FIG. 10 can continue through the duration of the arming sequence. Once needle assembly (20) is armed as shown in block (436) of FIG. 7, indicators (320, 322, 324) can switch to the state shown schematically in block (438) of FIG. 7 and schematically in FIG. 11. In this state, proximal indicator (320) and intermediate indicator (322) are both switched to an off state. Meanwhile, distal indicator (324) is switched to a solid or continuous illumination state. In this state, indicators (320, 322, 324) communicate to an operator that the arming sequence is complete and biopsy device (10) is ready for sample acquisition.

Figure 11:
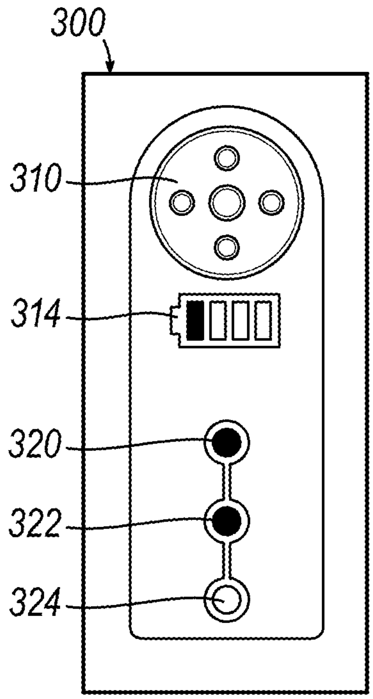
FIG. 11 depicts yet another detailed top plan view of the user interface of FIG. 6, in a fourth state.
Figure 12:
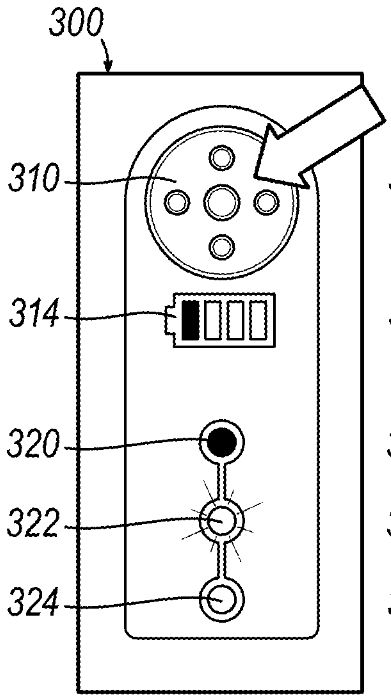
FIG. 12 depicts yet another detailed top plan view of the user interface of FIG. 6, in a fifth state.

Once indicators (320, 322, 324) are activated as shown schematically in block (438) of FIG. 7 and graphically in FIG. 11, an operator can next position biopsy device (10) for acquisition of a tissue sample. In one use, this process may include scoring tissue, injecting therapeutics into a patient, immobilizing tissue, or otherwise preparing for insertion of needle assembly (20). Once all desired preparations have been made, an operator can position the distal end of needle assembly (20) adjacent to targeted tissue of a patient. Optionally, this can also include inserting a portion of needle assembly (20) into a patient.

Once needle assembly (20) is positioned as desired, firing can be initiated by pressing actuator (310) as shown in block (440) of FIG. 7. At this stage, drive assembly (100) and/or firing assembly (140) can be activated to fire piercer (22) distally through tissue of a patient. Once actuator (310) is pressed, indicators (320, 322, 324) activate as shown schematically in block (444) of FIG. 7 and graphically in FIG. 12 for the duration of piercer (22) firing. In particular, proximal indicator (320) can be switched off, intermediate indicator (322) can be switched to a flashing or blinking state, and distal indicator (324) can be switched to an illuminated or solid state. Thus, it should be understood that the state of indicators (320, 322, 324) shown schematically in block (444) of FIG. 7 and graphically in FIG. 12 corresponds to the process of piercer (22) firing.

Figure 13:
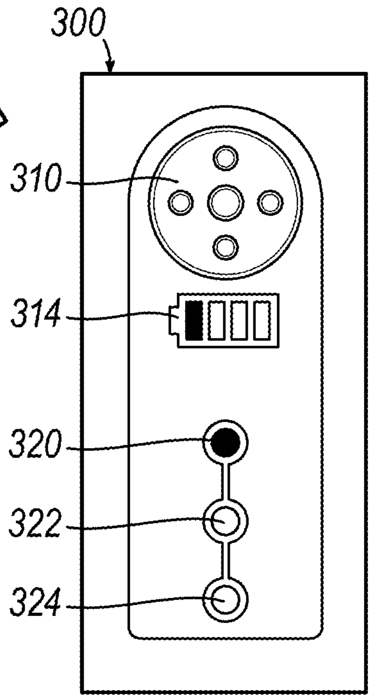
FIG. 13 depicts yet another detailed top plan view of the user interface of FIG. 6, in a sixth state.
Figure 14:
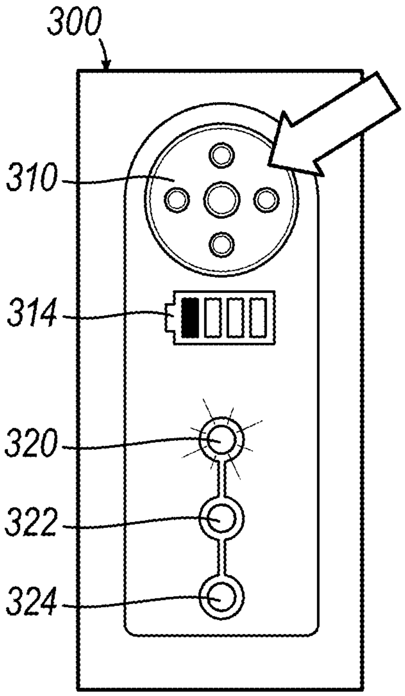
FIG. 14 depicts yet another detailed top plan view of the user interface of FIG. 6, in a seventh state.

Once piercer (22) has fired as shown in block (446), indicators (320, 322, 324) automatically switch to the state show schematically in block (448) of FIG. 7 and graphically in FIG. 13. As can be seen, in this state, proximal indicator (320) can be switched off, while intermediate indicator (322) and distal indicator (324) can be switched to an illuminated or solid state. Thus, it should be understood that the state of indicators (320, 322, 324) shown schematically in block (448) of FIG. 7 and graphically in FIG. 13 communicates completion of piercer (22) firing to an operator.

Once piercer (22) firing is complete, an operator can next begin collection of a tissue sample. To begin collection of a tissue sample, an operator can press actuator (310) as shown in block (450) of FIG. 7. Once actuator (310) is pressed, drive assembly (100) and or firing assembly (140) can be activated to fire cutter (40) distally. This movement causes distal end (42) of cutter (40) to sever a tissue sample into notch (26) of piercer. In some uses, severing of the tissue sample may be additionally facilitated by tissue naturally prolapsing into notch (26) prior to, or during, advancement of cutter (40). Simultaneously, indicators (320, 322, 324) automatically switch to the state show schematically in block (454) of FIG. 7 and graphically in FIG. 14. As can be seen, in this state, proximal indicator (320) can be switched to a flashing or blinking state, while intermediate indicator (322) and distal indicator (324) can be switched to an illuminated or solid state. Thus, it should be understood that the state of indicators (320, 322, 324) shown schematically in block (454) of FIG. 7 and graphically in FIG. 14 communicates to an operator that cutter (40) firing and the process of sample accusation is in progress. This state can continue until sample acquisition is complete.

After cutter (40) has fired, sample acquisition continues by activating drive assembly (100) and/or firing assembly (140) to retract piercer (22) proximally while cutter (40) remains in position. This proximal retraction of piercer (22) draws the severed tissue sample proximally to tissue sample holder (200), where the severed tissue sample can be collected by tissue sample holder (200) or any other tissue sample collection means using the process described above. For instance, shaft (242) can be rotated using keyed portion (244) to rotate wipers (250) and thereby extract the tissue sample from notch (26). Once the tissue sample is extracted from notch (26), piercer (22) can then be advanced distally to return to its original position prior to arming shown in block (430) or after initialization shown in block (420).

Figure 15:
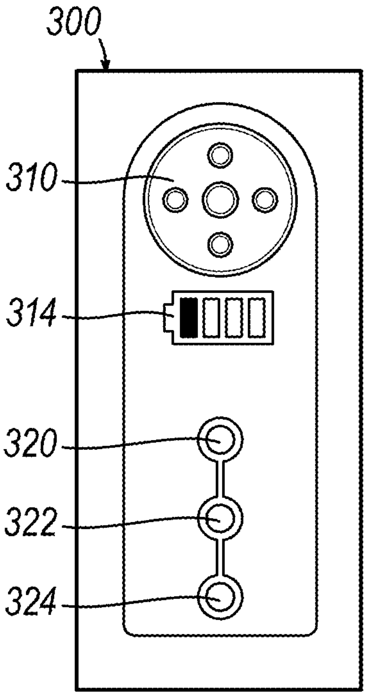
FIG. 15 depicts yet another detailed top plan view of the user interface of FIG. 6, in an eighth state.

After sample collection is complete as shown by block (456) in FIG. 7, indicators (320, 322, 324) automatically switch to the state show schematically in block (458) of FIG. 7 and graphically in FIG. 15. As can be seen, in this state, proximal indicator (320), intermediate indicator (322), and distal indicator (324) can all be switched off. Thus, it should be understood that the state of indicators (320, 322, 324) shown schematically in block (458) of FIG. 7 and graphically in FIG. 15 communicates to an operator that cutter (40) firing and the process of sample accusation has completed.

Once sample acquisition has completed, biopsy device (10) is ready to collect additional samples as shown in block (460). At this stage, further additional samples can optionally be collected by pressing actuator (310) again and returning to block (430) of FIG. 7. In some examples, this may include an intermediate step of manipulating shaft (242) of tissue sample holder (200) to reposition any previously collected tissue samples as desired. The process described above is then repeated again starting at block (430). Alternatively, if a desired number of samples have been collected, needle assembly (20) can be removed from the patient and the biopsy procedure can be finalized.

Figure 16:
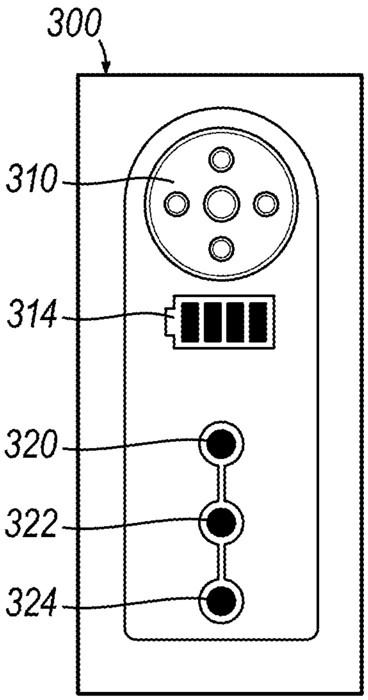
FIG. 16 depicts yet another detailed top plan view of the user interface of FIG. 6, in a ninth state.
Figure 17:
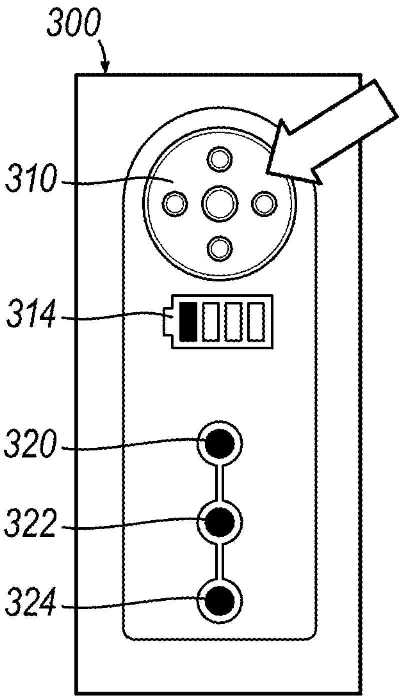
FIG. 17 depicts yet another detailed top plan view of the user interface of FIG. 6, in a tenth state.

FIGS. 16 and 17 show certain alternative states for indicators (320, 322, 324) that can be used in addition to the states described above. For instance, FIG. 16 shows a state of indicators (320, 322, 324) that can correspond to when the probe is detached from the holster of biopsy device (10). In this state, all indicators (320, 322, 324) are set to an off state. In addition, power indicator (314) is also set to an off state. In some uses, this state may be desirable to conserve power while biopsy device (10) is not in use.

FIG. 17 shows an alternative state to the state shown in FIG. 16. In this state, probe can still be detached from holster. However, it still may nonetheless be desirable for an operator to obtain input from power indicator (314). To do so, an operator may press actuator (310) while holster is detached from probe and user interface is in the state shown in FIG. 16. Once actuator (310) is pressed, power indicator (314) can activate to communicate to an operator the level of power remaining in holster of biopsy device (10). Meanwhile, indicators (320, 322, 324) remain in the off state. After actuator (310) is pressed, power indicator (314) can remain on for a predetermined period of time. Alternatively, power indicator (314) can remain on indefinitely until either actuator (310) is pressed again or a probe is attached to holster.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A core needle biopsy device, comprising: a needle assembly, wherein the needle assembly includes a piercer and a hollow cutter, wherein the piercer includes a sharp distal tip and a notch proximal to the distal tip, wherein the piercer is slidably disposed within the cutter to sever a tissue sample into the notch of the piercer; a drive assembly configured to selectively move the piercer and the cutter; and a user interface having a plurality of indicators, wherein each indicator of the plurality of indicators is configured to independently transition between a plurality of predetermined states to collectively define a plurality of predetermined status sequences that indicate movement of the piercer and the cutter via the drive mechanism.

Example 2

The core needle biopsy device of Example 1, wherein the user interface includes three indicators.

Example 3

The core needle biopsy device of Examples 1 or 2, wherein each indicator of the plurality of indicators is configured to transition between a continuously on state, a flashing state, and an off state.

Example 4

The core needle biopsy device of any one or more of Examples 2 through 3, wherein the plurality of indicators are arranged along an axis parallel relative to the piercer.

Example 5

The core needle biopsy device of any one or more of Examples 1 through 4, wherein the drive assembly is configured to move the piercer and the cutter through a predetermined initialization sequence, wherein each indicator of the plurality of indicators is configured to transition to a first predetermined state during the initialization sequence.

Example 6

The core needle biopsy device of Example 5, wherein each indicator of the plurality of indicators is configured to transition to a second predetermined state after completion of the initialization sequence.

Example 7

The core needle biopsy device of any one or more of Examples 1 through 4, wherein the drive assembly is configured to move the piercer and the cutter through a predetermined arming sequence, wherein each indicator of the plurality of indicators is configured to transition to a first predetermined state during the arming sequence.

Example 8

The core needle biopsy device of Example 7, wherein each indicator of the plurality of indicators is configured to transition to a second predetermined state after completion of the arming sequence.

Example 9

The core needle biopsy device of any one or more of Examples 1 through 4, wherein the drive assembly is configured to move the piercer and the cutter through a predetermined sample acquisition sequence, wherein each indicator of the plurality of indicators is configured to transition to a first predetermined state during the arming sequence.

Example 10

The core needle biopsy device of Example 9, wherein each indicator of the plurality of indicators is configured to transition to a second predetermined state after completion of the sample acquisition sequence.

Example 11

The core needle biopsy device of Example 9, wherein the sample accusation sequence includes firing the piercer, the cutter, or the piercer and the cutter together.

Example 12

A user interface incorporated into a core needle biopsy device, wherein the user interface includes an actuator in communication with one or more features of the biopsy device, and an indicator array, wherein the indicator array includes a first indicator, a second indicator, a third indicator, wherein each of the first indicator, the second indicator, and the third indicator is configured to transition between a first state, a second state, and a third state to define a plurality of predetermined status sequences corresponding to an operational status of the core needle biopsy device.

Example 13

The user interface of Example 12, wherein the plurality of status sequences includes an initialization status sequence, an arming status sequence, a first firing sequence, and a second firing sequence, wherein each status sequence is unique relative to each other status sequence.

Example 14

The user interface of Examples 12 or 13, wherein each of the first indicator, the second indicator, and the third indicator is configured to automatically transition between the first state, the second state, and the third state in response to operator interaction with the actuator.

Example 15

The user interface of any one or more of Examples 12 through 14, wherein each of the first indicator, the second indicator, and the third indicator is configured to automatically transition between the first state, the second state, and the third state in response to operation of the biopsy device.

Example 16

The user interface of any one or more of Examples 12 through 15, wherein the first state corresponds to a given indicator being off, wherein the second state corresponds to a given indicator being continuously on, wherein the third state corresponds to a given indicator being intermittently on.

Example 17

The user interface of any one or more of Examples 12 through 16, further comprising a power indicator, wherein the power indicator is configured to communicate a power status of the biopsy device to an operator.

Example 18

The user interface of any one or more of Examples 12 through 17, wherein the indicator array comprises a single LED screen, wherein each of the first indicator, the second indicator and the third indicator is formed by a segment of the LED screen.

Example 19

The user interface of any one or more of Examples 12 through 17, wherein each of the first indicator, the second indicator, and the third indicator is an LED.

Example 20

A method for collecting a tissue sample using a biopsy device, the method comprising: arming the biopsy device by retracting a piercer and a cutter proximally relative to a probe and holster of the biopsy device; indicating the step of arming using an indicator array by adjusting a plurality of indicators of the indicator array to a predetermined first status sequence; firing one or more of the piercer or the cutter; indicating the step of firing by adjusting the plurality of indicators of the indicator array to a predetermined second status sequence different from the first status sequence; acquiring a tissue sample using the piercer and the cutter; and indicating the step of acquiring by adjusting the plurality of indicators of the indicator array to a predetermined third status sequence different from the first and second status sequences.

Example 21

The method of Example 20, wherein the step of firing includes firing the piercer, wherein the step of acquiring a tissue sample includes firing the cutter.

Example 22

The method of Examples 20 or 21, further comprising the step of detaching the probe from the holster; and indicating detachment of the probe from the holster by adjusting the plurality of indicators of the indicator array to a predetermined third status sequence different from the first, second, and third status sequences.

Example 23

The method of Example 22, further comprising the step of indicating a power level associated with the holster using a power indicator by pressing a button associated with the indicator array.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A core needle biopsy device, comprising:

(a) a needle assembly, the needle assembly including a piercer and a hollow cutter, the piercer including a sharp distal tip and a notch proximal to the distal tip, the piercer being slidably disposed within the cutter to sever a tissue sample into the notch of the piercer;

(b) a drive assembly configured to selectively move the piercer and the cutter; and (c) a user interface having a plurality of indicators, the plurality of indicators including three light emitting diodes (LEDs), adjacent to each other and aligned with the needle assembly along a longitudinal axis of the core needle biopsy device, each indicator of the plurality of indicators being configured to:

(i) operate in a predetermined state from a plurality of predetermined states including an off state, a solid state, and a flashing state, and (ii) independently transition between the plurality of predetermined states, the combination of the predetermined state for each of the plurality of indicators defining a predetermined status sequence from a plurality of predetermined status sequences, each of the plurality of predetermined status sequences paired with an operational status of the biopsy device from a plurality of operational statuses to indicate the operational status, each of the plurality of predetermined status sequences paired with a single operational status from the plurality of operational statuses, and each of the plurality of operational statuses paired with a single predetermined status sequence from the plurality of predetermined status sequences, at least one of the plurality of operational statuses indicating operating both the piercer and the cutter via the drive assembly, the plurality of operational statuses including a cocking sequence, a piercer firing sequence, and a cutter firing sequence, the three LEDs collectively transitioning through different combinations of the off state, the solid state, and the flashing state during and after each of the cocking sequence, the piercer firing sequence, and the cutter firing sequence to indicate progress through the plurality of operational statuses.

2. The core needle biopsy device of claim 1, the drive assembly being configured to move both the piercer and the cutter through a predetermined initialization sequence, each indicator of the plurality of indicators being configured to transition to a first predetermined state during the initialization sequence.

3. The core needle biopsy device of claim 2, each indicator of the plurality of indicators being configured to transition to a second predetermined state after completion of the initialization sequence.

4. The core needle biopsy device of claim 1, the drive assembly being configured to move both the piercer and the cutter through a predetermined arming sequence, each indicator of the plurality of indicators being configured to transition to a first predetermined state during the arming sequence.

5. The core needle biopsy device of claim 4, each indicator of the plurality of indicators being configured to transition to a second predetermined state after completion of the arming sequence.

6. The core needle biopsy device of claim 1, the drive assembly being configured to move both the piercer and the cutter through a predetermined sample acquisition sequence, each indicator of the plurality of indicators being configured to transition to a first predetermined state during the arming sequence.

7. The core needle biopsy device of claim 6, each indicator of the plurality of indicators being configured to transition to a second predetermined state after completion of the sample acquisition sequence.

8. The core needle biopsy device of claim 6, the sample acquisition sequence including firing the piercer, the cutter, or the piercer and the cutter together.

9. A method for collecting a tissue sample using a biopsy device, the method comprising:

(a) arming the biopsy device by retracting a piercer and a cutter proximally relative to a probe and holster of the biopsy device;
(b) indicating the step of arming using a light emitting diode (LED) array by adjusting a plurality of LEDs of the LED array to a predetermined first status sequence;
(c) firing the piercer;
(d) indicating the step of firing the piercer by adjusting the plurality of LEDs of the LED array to a predetermined second status sequence different from the first status sequence;
(e) firing the cutter;
(f) indicating the step of firing the cutter by adjusting the plurality of LEDs of the LED array to a predetermined third status sequence different from the first status sequence and the second status sequence;
(g) acquiring a tissue sample using the piercer and the cutter; and
(h) indicating the step of acquiring by adjusting the plurality of LEDs of the LED array to a predetermined fourth status sequence different from the first, second, and third status sequences;

the LED array comprising three LEDs, each LED of the LED array:
(i) operable between states comprising a continuously on state, a flashing state, and an off state, and
(ii) combining to define each of the first predetermined status sequence, the second predetermined status sequence, the third predetermined status sequence, and the fourth predetermined status sequence based on a unique combination of states, the three LEDs collectively transitioning through different combinations of the continuously on state, the flashing state, and the off state during and after each of the arming step, the piercer firing step, the cutter firing step, and the acquiring step to indicate progress through the method, each of the arming step and firing steps initiated by actuating a single common actuator.

10. The method of claim 9, the single common actuator being a single button.

11. The method of claim 10, further comprising initiating the step of acquiring the tissue sample using the single button.

12. The method of claim 11, the single button being pressed to initiate the steps of arming the biopsy device, firing the piercer or the cutter, and acquiring the tissue sample in sequential order.

13. A core needle biopsy device, comprising:
(a) a needle assembly, the needle assembly including a piercer and a hollow cutter, the piercer including a sharp distal tip and a notch proximal to the distal tip, the piercer being slidably disposed within the cutter to sever a tissue sample into the notch of the piercer;
(b) a drive assembly configured to selectively move the piercer and the cutter; and
(c) a user interface having a single button and three light emitting diodes (LEDs) including a first LED, a second LED, and a third LED, the single button operable between states comprising an actuated state and a non-actuated state, the single button being configured to initiate movement of the drive assembly through a plurality of predetermined operational sequences based on a change in state of the single button and a predetermined operational sequence from the plurality of predetermined operational sequences, each LED being configured to independently transition between a plurality of predetermined states comprising a flashing state, a solid state, and an off state, the three LEDs combining to collectively indicate an operational status with respect to each of the plurality of predetermined operational sequences, wherein:
(i) the first LED is in the off state, the second LED is in the off state, and the third LED is in the flashing state when the operational sequence is a cocking sequence;
(ii) the first LED is in the off state, the second LED is in the off state, and the third LED is in the solid state to indicate the cocking sequence is complete;
(iii) the first LED is in the off state, the second LED is in the flashing state, and the third LED is in the solid state when the operational sequence is a piercing firing sequence;
(iv) the first LED is in the off state, the second LED is in the solid state, and the third LED is in the solid state to indicate the piercing firing sequence is complete;
(v) the first LED is in the flashing state, the second LED is in the solid state, and the third LED is in the solid state when the operational sequence is a cutting firing sequence; and
(vi) the first LED is in the solid state, the second LED is in the solid state, and the third LED is in the solid state to indicate the cutting firing sequence is complete.

14. The core needle biopsy device of claim 13, the plurality of predetermined operational sequences of the drive assembly further includes an initialization sequence, the single button being configured to initiate each of the initialization sequence, the cocking sequence, the piercing firing sequence, and the cutting firing sequence.

15. The core needle biopsy device of claim 14, the plurality of predetermined operational sequences of the drive assembly further including a sample acquisition sequence, the single button being further configured to initiate the sample acquisition sequence.

16. The core needle biopsy device of claim 15, the single button being configured to initiate the initialization sequence, the cocking sequence, the piercing firing sequence, the cutting firing sequence, and the sample acquisition sequence in a fixed sequence in the order of the initialization sequence, the cocking sequence, the piercing firing sequence, the cutting firing sequence, and the sample acquisition sequence.

17. The core needle biopsy device of claim 15, the initialization sequence, the cocking sequence, the piercing firing sequence, the cutting firing sequence, and the sample acquisition sequence corresponding to the piercer and the cutter moving through one or more predetermined movements via the drive assembly.

* * * * *